United States Patent
Chen et al.

(10) Patent No.: US 8,247,444 B2
(45) Date of Patent: *Aug. 21, 2012

(54) ANTI-TUMOR EFFECT OF DIMERIC PHTHALIDE COMPOUND

(75) Inventors: Fei Chen, Shanghai (CN); Tao Wang, Shanghai (CN); Yifeng Wu, Shanghai (CN)

(73) Assignees: Fei Chen, Shanghai (CN); Tao Wang, Shanghai (CN)

( * ) Notice: Subject to any disclaimer, the term of this patent is extended or adjusted under 35 U.S.C. 154(b) by 328 days.

This patent is subject to a terminal disclaimer.

(21) Appl. No.: 12/523,792

(22) PCT Filed: Jan. 19, 2007

(86) PCT No.: PCT/CN2007/000205
§ 371 (c)(1),
(2), (4) Date: Jul. 20, 2009

(87) PCT Pub. No.: WO2008/089594
PCT Pub. Date: Jul. 31, 2008

(65) Prior Publication Data
US 2010/0010081 A1 Jan. 14, 2010

(51) Int. Cl.
*A01N 43/12* (2006.01)
*A01N 43/26* (2006.01)
*A01N 43/08* (2006.01)
*A61K 31/34* (2006.01)
*A61K 31/335* (2006.01)

(52) U.S. Cl. ........................................ 514/462; 514/468
(58) Field of Classification Search .................. 514/462, 514/468
See application file for complete search history.

(56) References Cited

FOREIGN PATENT DOCUMENTS
| | | | |
|---|---|---|---|
| CN | 1679544 | A | 10/2005 |
| JP | 9-77666 | A | 3/1997 |
| WO | WO 2006/107273 | A1 | 10/2006 |

OTHER PUBLICATIONS

CN1679544 Chinase Patent Abstract, pp. 1-2.*
Tsai et al. (Journal of Neurochemistry, 2006, vol. 99, pp. 1251-1262.*
International Search Report of PCT/CN2007/000205, dated Nov. 1, 2007.

* cited by examiner

*Primary Examiner* — Samira Jean-Louis
(74) *Attorney, Agent, or Firm* — Hamre, Schumann, Mueller & Larson, P.C.

(57) ABSTRACT

The present invention provides for the use of a dimeric phthalide compound, the dimeric phthalide compound has broad anti-tumor activity, can directly inhibit the proliferation of tumor cells and induce cell death, but also indirectly inhibit the development of tumors by suppressing neovascularization. And further, the dimeric phthalide compound can be used alone or in combination to treat cancer, as well as in combination with chemotherapeutics to increase the efficacy of chemotherapeutics and decrease the toxicity of chemotherapeutics.

10 Claims, 7 Drawing Sheets

A

B

ANTI-TUMOR EFFECT OF DIMERIC PHTHALIDE COMPOUND

FIELD OF THE INVENTION

The invention relates to medical and pharmaceutical fields, particularly relates to the use of a dimeric phthalide compound, the dimmer can be used alone or in combination for preparation of anti-tumor drugs.

BACKGROUND OF THE INVENTION

The statistical data from World Health Organization (WHO) shows that, about 10 million people occur cancer and 7 million die, which makes cancer become the second leading cause of death around the world, second only to cardiovascular disease. Currently, clinically used chemotherapeutics mainly are cytotoxic medications, which killing cancer cells as well as normal cells. Although significant developments have been obtained in some leukocythemia diseases for which virulence gene is single, the effect of chemotherapeutics are limited and its side effects are obvious. And therefore, it has been always interested in developing an anti-cancer prodrug from natural animals or plants with low toxicity, high potency, definitive target and new mechanism for scientists and researchers domestic as well as abroad.

It has been confirmed through thousand years of medical practices in Chinese medicine, there is a growing number of people who recognize and utilize the Chinese medicine worldwide. Recently, there has been great progress in the research for anti-cancer active ingredients from Chinese medicine, and has found some ingredients that can suppress or kill tumor cells.

Because there is a great variety of Chinese medicine and its active ingredients are complex, however, our knowledge about these anti-cancer active ingredients is still very little. And therefore, there is a continued need to separate from Chinese medicine and study those active ingredients effective for cancer, in seeking of a low-toxicity, anti-drug resistance active ingredient which can suppress and kill tumor cells through multi-targets or multi-pathways.

SUMMARY OF THE INVENTION

The object of the present invention is to provide a compound having excellent anti-tumor potency.

In the first aspect, the present invention provides the use of a dimeric phthalide compound of formula (I) in the manufacture of anti-tumor composition,

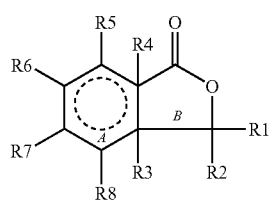

(I)

wherein,
R1 represents H, hydroxyl, C1-C8 alkyl, C2-C8 alkenyl, C2-C8 alkynyl, C3-C8 cycloalkyl, C1-C8 alkoxyl, C1-C4 carboxyl, halogen;

R2 is absent or represents H, hydroxyl, C1-C8 alkyl, C2-C8 alkenyl, C2-C8 alkynyl, C3-C8 cycloalkyl, C1-C8 alkoxyl, C1-C4 carboxyl, halogen;

R3 or R4 independently represents H, hydroxyl, C1-C8 alkyl, C2-C8 alkenyl, C2-C8 alkynyl, C3-C8 cycloalkyl, C1-C8 alkoxyl, halogen;

R5 or R8 independently represents H, hydroxyl, C1-C8 alkyl, C2-C8 alkenyl, C2-C8 alkynyl, C3-C8 cycloalkyl, C1-C8 alkoxyl, C1-C4 carboxyl, phenyl, aryl, aralkyl, 5- or 6-membered heterocycle containing 1-2 nitrogen atoms, halogen;

R6 or R7 independently represents H, hydroxyl, C1-C8 alkyl, C2-C8 alkenyl, C2-C8 alkynyl, C1-C4 carboxyl, halogen; or R6 together with R7 to form a 5-7 membered ring;

◯ represent A ring containing 1-3 double bonds;

wherein, the alkyl, alkenyl, alkynyl, cycloalkyl, alkoxyl, phenyl, aryl, aralkyl and heterocycle contain 0-3 substituents selected from the group consisting of C1-C3 alkyl, hydroxyl, halogen.

In a preferred embodiment of the present invention, the phthalide compound has the following sruture:

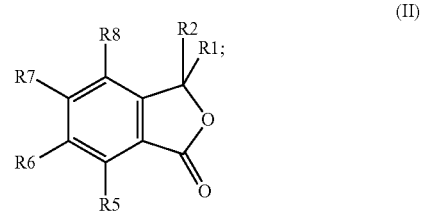

(II)

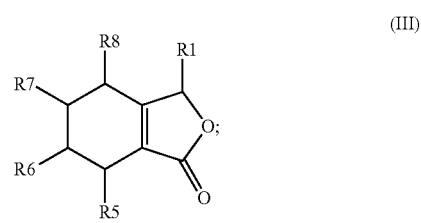

(III)

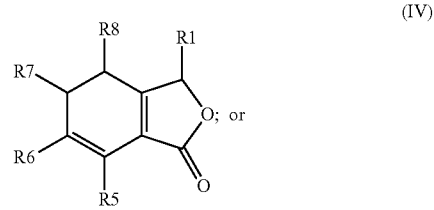

(IV)

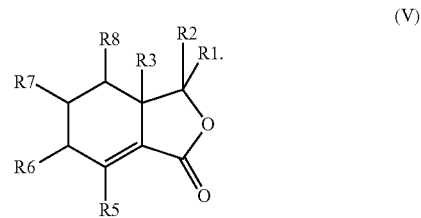

(V)

wherein, R1~R8 are defined as above.

In another preferred embodiment of the present invention, the dimeric phthalide compound has the following structure:

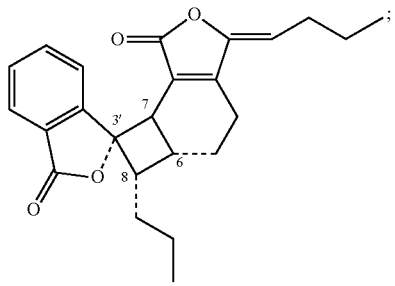
(1)
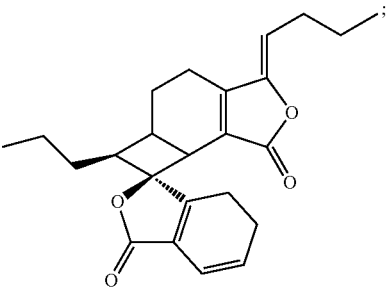
(6)
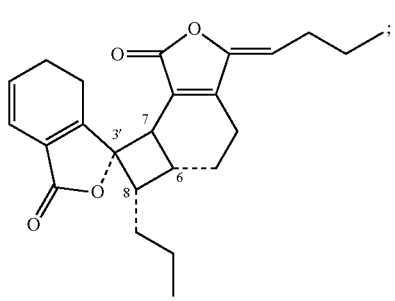
(2)
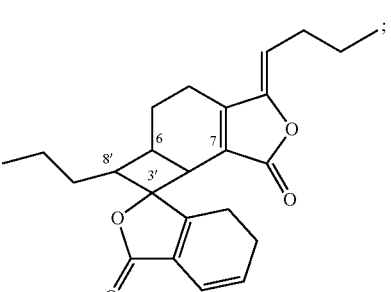
(7)
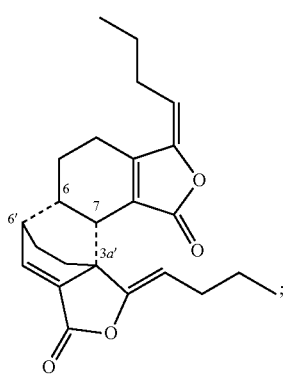
(3)
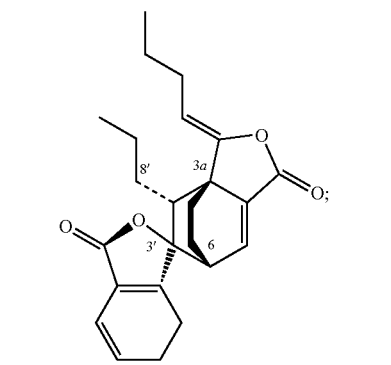
(8)
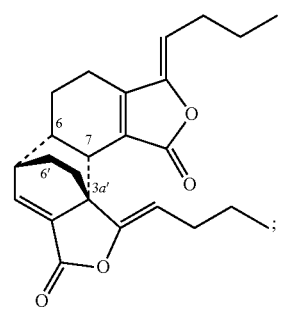
(4)
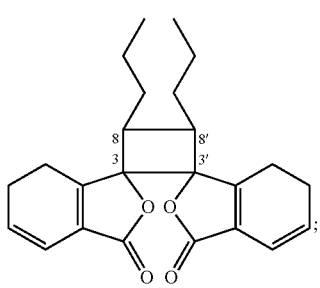
(9)
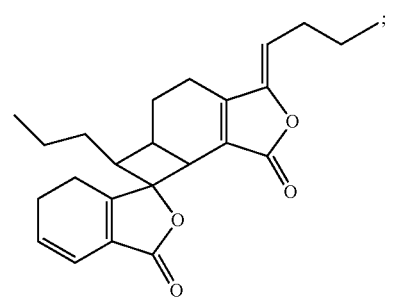
(5)
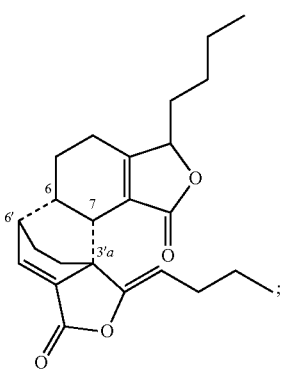
(10)

(11)
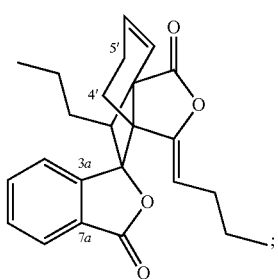
(12)
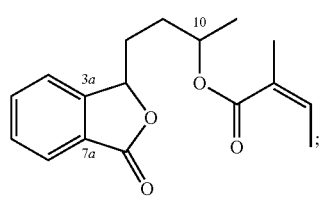
(13)
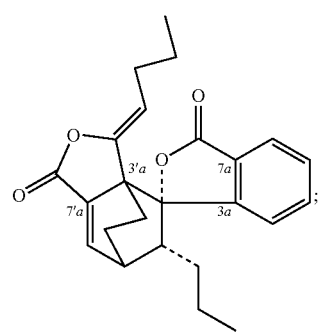
(14)
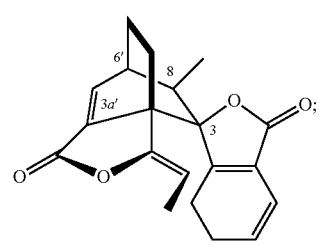
(15)
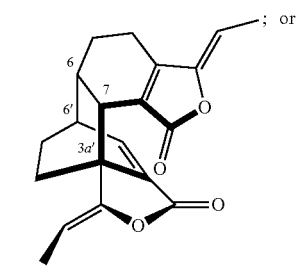; or
(16)
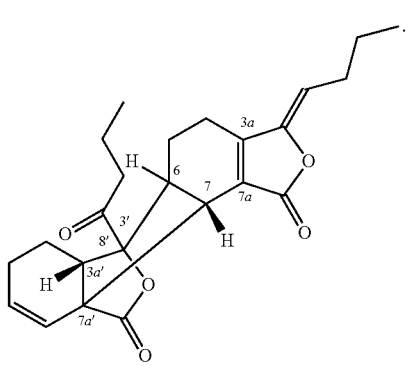
In another preferred embodiment of the present invention, the dimeric phthalide compound has the following structure:
(1)
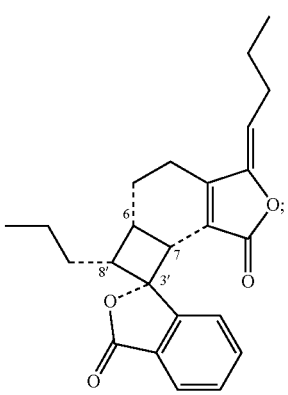
(3)
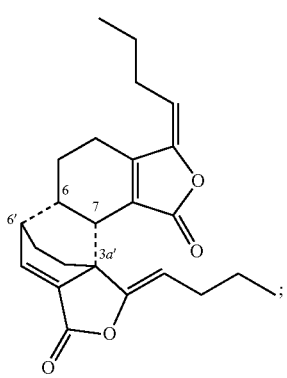;
(16)
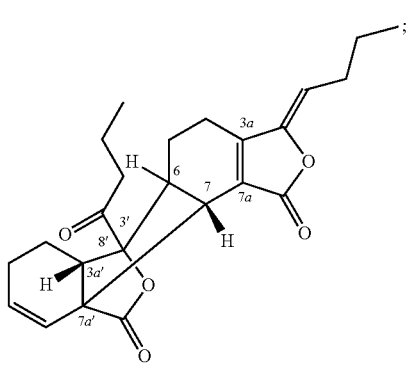;

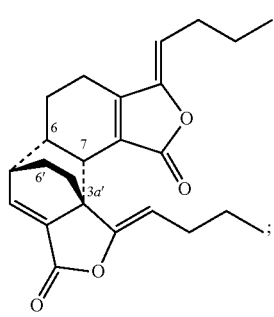

(4)

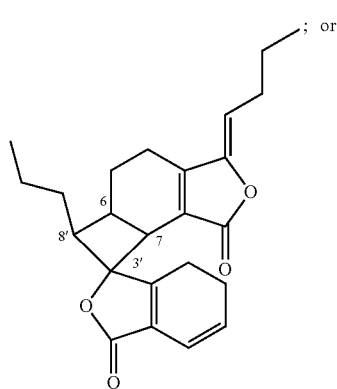

; or (7)

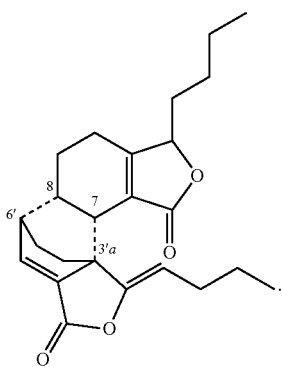

(10)

In another preferred embodiment of the present invention, the composition comprises two or more dimeric phthalide compounds.

In another preferred embodiment of the present invention, the anti-tumor composition may directly inhibit the proliferation of tumor cell or induce cell death, alternatively, the anti-tumor composition may indirectly inhibit the development of tumors by suppressing tumor neovascularization.

In another preferred embodiment of the present invention, the anti-tumor composition may induce Caspase dependent mitochondrion death pathway, or induce Caspase independent mitochondrion death pathway.

In another preferred embodiment of the present invention, the tumors are drug sensitive tumors, apoptosis resistance tumors or drug resistance tumors.

In another preferred embodiment of the present invention, the tumors may be selected from the group consisting of nonsmall-cell lung cancer, liver cancer, encephaloma, leukocythemia, carcinoma of prostate, intestine cancer, myeloma tumor, lymphoma, breast carcinoma, ovarian cancer, gastric cancer, small cell lung cancer, esophageal carcinoma, esophageal carcinoma, or sarcoma.

In another preferred embodiment of the present invention, the anti-tumor composition can be further used to promote the efficacy of chemotherapeutics, decrease the toxicity of the chemotherapeutics and/or resist tumor metastasis.

In another preferred embodiment of the present invention, the anti-tumor composition further comprises at least one another anti-tumor drug, for example chemotherapeutics.

In another preferred embodiment of the present invention, the another anti-tumor drug includes but not limited to the targeting drugs, such as gifitinib, erlotinib, sorafenib, bevacizumab; the cytotoxic drugs, such as vinblastines, anthracyclines, antibiotics, metabolic drugs; or differentiation inductors.

In the second aspect, the present invention provides the use of a dimeric phthalide compound of formula (I) in the manufacture of anti-tumor composition,

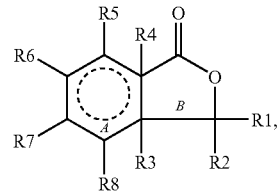

(I)

wherein, R1-R8 are defined as above.

In the third aspect, the present invention provides a method of treating tumor, comprising administering to a mammal in need thereof the dimeric phthalide compound of formula (I),

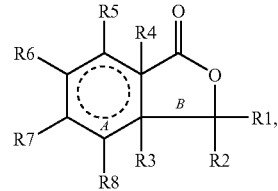

(I)

wherein, R1-R8 are defined as above.

In another preferred embodiment of the present invention, the dose of the dimeric phthalide compound is 1-400 mg/kg body weight, preferably 10-200 mg/kg body weight; further preferably 10-100 mg/kg body weight.

Other aspects of the present invention will be obvious for those skilled in the field through the description herein.

BRIEF DESCRIPTION OF THE DRAWINGS

FIG. 4A is flow cytometry graphs of U87, HL60 and H1299 after treating with S4 and S6, control represents the flow cytometry graph of various cell lines without treating with dimeric phthalide compounds; FIG. 4B is histograms of the H1299 cell cycle condition after treating with S1-S6 respectively, wherein the control represent the cell cycle condition of corresponding cells without treating with dimeric phthalide compounds.

FIG. 5A is the flow cytometry graph of HL60, H1299 and U251 after treating with different concentration of S1, S4 and S6 respectively; FIG. 5B shows the PI positive rate of HL60 after treating with S1-S6 (concentration 10 μg/mL, for 48 hours); FIG. 5C shows the PI positive rate of H1299 after treating with S1-S6 (concentration 20 μg/mL, for 48 hours); FIG. 5D shows the PI positive rate of U251 after treating with S1-S6 (concentration 10 μg/mL, for 48 hours). The control represents a corresponding result of cells without treating with dimeric phthalide compounds.

FIG. 8A shows the influence of S1-S6 on the angiogenesis of chicken embryo allantocherion observed under microscope, wherein the control represents the angiogenesis of chicken embryo allantocherion without treating with dimeric phthalide compound; FIG. 8B shows angiogenesis inhibition rate of different concentration of S1-S6 compounds.

MODES FOR CARRYING OUT THE INVENTION

Figure 1:
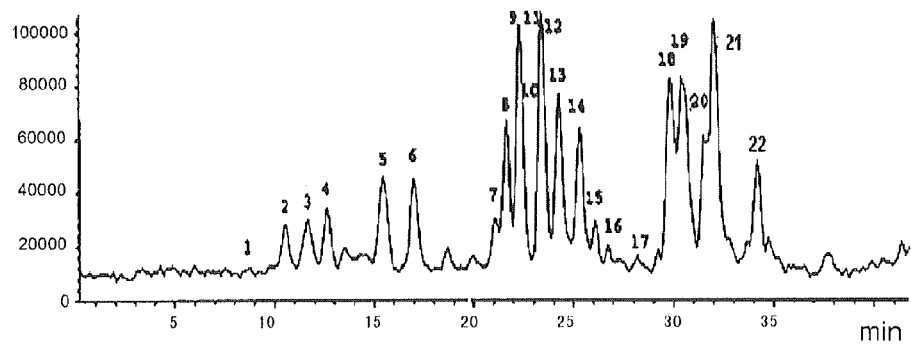
FIG. 1 shows the chromatogram of the phthalide compound or its dimer.

The present inventors found for the first time that the dimeric phthalide compound possess broad, extremely outstanding anti-tumor effect after extensive and deep investigation, and its anti-tumor effect was substantively better than the monomer of the phthalide compound. The present inventors also found that the dimeric phthalide compound can effectively damage various kinds of tumor through Caspase-dependent or independent mitochondrion pathway, and indirectly induce tumor decreasing through the inhibition of new vessels. In addition, the combination of the dimeric phthalide compound or its derivatives can substantively promote potency of the chemotherapeutics and decrease its side effects. Base on the above, the present invention was completed.

The term "alkyl" means any straight or branched chain saturated aliphatic hydrocarbon radical having 1-8 carbon atoms, preferably 1-6 carbon atoms; the alkyl may be branched, for example methyl group, ethyl group, n-propyl group, iso-propyl group, n-butyl group, iso-butyl group, t-butyl group, n-pentyl group, isopentyl group, t-pentyl group, hexyl group etc. The term "alkenyl" means any straight or branched chain hydrocarbon radical having at least one carbon-carbon double bond, and having 2-8 carbon atoms, preferably 2-6 carbon atoms. The term "alkynyl" means any straight or branched chain hydrocarbon radical having at least one carbon-carbon triple bond, and having 2-8 carbon atoms, preferably 2-6 carbon atoms.

The term "aryl" means an aromatic system, which can be monocyclic groups, as well as fused groups or connected together to form multi-aromatic radicals, so that some of the fused or connected ring forming conjugated aromatic system. Aryl includes but not limited to phenyl, naphthyl, tetrahydronaphthyl.

The term "cycloalkyl" means any cyclic alkyl group having 3-8 carbon atoms, such as cyclopropy, cyclopentyl, cyclohexyl and cycloheptyl.

The term "alkoxyl" means any alkoxyl having 1-8 carbon atoms, such as methoxyl, ethoxyl, propoxy, butyloxy, pentyloxy, hexyloxy, and the like.

The term "heterocycle" means stable monocyclic group having 4-7 members, preferably 5-6 members or stable multi-cyclic heterocycle, the heterocycle can be saturated, partially unsaturated or unsaturated, and consisting of carbon atoms and 1-4 hetero atoms selected from the group consisting of N, O and S, N and S can be oxidized. The heterocycle can further include any multi-cycle, in which any one of the above heterocycle may be fused to aromatic ring.

The term "substituted aryl" or "substituted heterocycle" means aryl or heterocycle which has been substituted with 1-3 groups selected from the group consisting of halogen, CN, OH, $NO_2$, amino, alkyl, cycloalkyl, alkenyl, alkynyl, alkoxyl, arylxoy, substituted alkoxyl, alkyl carbony, alkyl carboxyl, alkylamino or arylthio. Preferably, the substituent is halogen, C1-C4 alkyl, alkyl, hydroxyl.

The term "halogen" means halo element, such as F, Cl, Br or I.

The Active Ingredient

The anti-tumor active ingredient according to the present invention is a dimeric phthalide compound of formula (I):

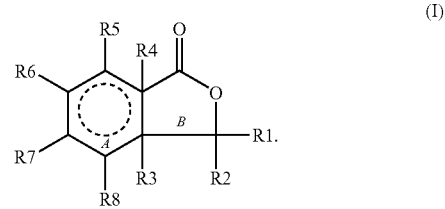

(I)

The dimeric phthalide compound of the present invention can synthesized or separated from nature. For example, the dimeric phthalide compound can be directly extracted from Umbelliferae plant angelica or chuanxiong rhizome; or the monomer of the phthalide compound or its derivatives can be extracted from angelica or chuanxiong rhizome, and then polymerized into dimer; or it can be prepared through total synthesis. The two monomers of the resultant dimer (having the structure of formula (I)) can be same or different.

The anti-tumor effect of the dimeric phthalide compound was substantively better than that of phthalide compound monomer, which need lower dose to attain similar effects.

Usage

The present invention provides the use of a dimeric phthalide compound in the manufacture of anti-tumor compositions.

The dimeric phthalide compound of the present invention can induce cell death through Caspase dependent or independent mitochondrion pathway, and can be used to suppress or kill tumor cells, especially apoptosis resistance tumors or drug resistance tumors, which were described in details in the Examples. And meanwhile, because the dimeric phthalide compound possesses significant inhibition effect on neovascularization, it can indirectly suppress the development and metastasis of tumor through inhibiting the formation of new vessels.

In addition, the dimeric phthalide compound can be used to promote the potency of another anti-tumor medication such as chemotherapeutics, and/or decrease the toxicity of the chemotherapeutics. Since the dimeric phthalide compound increases the efficacy of the chemotherapeutics and/or decreases the toxicity of the same by acting on the tumor cells, it is effective for various kinds of chemotherapeutics. The chemotherapeutics include but not limited to the targeting drugs, such as Gifitinib, Erlotinib, Sorafenib, Bevacizumab and the like; the cytotoxic drugs, such as Vinblastines, Anthracyclines, antibiotics, metabolic drugs; or differentiation inductors and the like.

The Pharmaceutical Composition

The present invention also provides a pharmaceutical composition, comprising a dimeric phthalide compound as active ingredient together with one or more pharmaceutical acceptable carriers or excipients such as solvents and dilutions. The term "pharmaceutical acceptable" ingredient refers to substances which are suitable for human and/or animal without undue adverse effects such as toxicity, stimulation and allergy, and have a reasonable benefit/risk ratio. The pharmaceutical acceptable carriers used in the present invention include various kinds of conventional solid and liquid carriers. For example, the solid carriers may include starch, lactose, calcium phosphate dibasic, microcrystalline cellulose and the like, the liquid carriers may include sterile water, polyethylene glycol and the like, as long as it is suitable for the property of active ingredients and desirable administration mode.

The composition according to the present invention can be made into various conventional forms, such as tablets, capsules, dispensable powders, granules or suspensions, syrups (for example, containing about 10-50% sugar), and elixirs (containing about 20-50% ethanol), or parenteral forms such as sterile injectable solutions or suspensions (containing about 0.05-5% suspending agent in the isotonic media). For example, the pharmaceutical formulations may contain about 0.01-99.9 wt %, preferably 2.5-90 wt %, more preferably 5-60 wt % active ingredient mixed with carriers.

The present composition contains a single dimeric phthalide compound, or optionally contains more than one of the dimeric phthalide compounds.

Another optional pharmaceutical composition may additionally contain other anti-tumor drugs such as chemotherapeutics, for example contains (a) 0.01-99 wt % (preferably 0.1-90 wt %) the dimeric phthalide compound; (b) 0.01-99 wt % (preferably 0.1-90 wt %) anti-tumor drugs; and (c) pharmaceutical acceptable carriers. Usually, the weight ratio of the component (a) to the component (b) is 1:100~100:1, preferably 10:1~1:10.

The pharmaceutical composition may further contain other additives such as pigments, preservatives and antioxidants and the like.

The effective dose of the active ingredient used in the invention may vary with the administration scheme and the severity of the disease to be treated. Generally, we can obtain satisfactory effects when the ingredient is administered with the dose of about 1-400 mg/kg body weight per day, preferably in 2-4 divided dosage forms daily, or as sustained dosage forms. The inventors have found practically, in the process of treatment, favorable anti-tumor effects can be obtained with low amount of the present dimeric phthalide compound, commonly the desired amount is 2-200 mg/kg body weight; more preferably 10-100 mg/kg body weight.

Treat Method

The present invention also provides a method of treating tumors, comprising administering to a mammal in need thereof a safe and effective amount of dimeric phthalide compounds. The "safe and effective amount" refers to an amount which can produce effects or actions on humans and/or animals and meanwhile being accepted by humans and/or animals. Preferably, the method may further comprise another anti-tumor drug or another treatment measure such as chemotherapy in combination.

The dimeric phthalide compound can be used alone or in combination for various tumors. The representative examples include but not limited to nonsmall-cell lung cancer, liver cancer, encephaloma, leukocythemia, carcinoma of prostate, intestine cancer, myeloma tumor, lymphoma, breast carcinoma, ovarian cancer, gastric cancer, small cell lung cancer, esophageal carcinoma, esophageal carcinoma, or sarcoma.

There exist no special limitations on the administration mode of the dimeric phthalide compounds. The compounds can be administered orally as well as intravenously, intramuscularly, topically, intratumorally or subcutaneously. The preferred administration mode is by oral, intravenous or intratumoral.

The Main Advantage of the Present Invention (1) It is found for the first time that the dimeric phthalide compound has broad and extremely excellent inhibition or killing effect on tumor cells, its anti-tumor effects are far better than phthalide compound monomers, and the dimeric phthalide compound could effectively damage various tumor cells through mitochondrion pathway.

(2) It is found for the first time that the dimeric phthalide compound has substantive inhibition effect on vascular proliferation, so as to inhibit indirectly the tumor proliferation.

(3) The dimeric phthalide compound combined with chemotherapeutics can substantively promote the efficacy of the chemotherapeutics and decrease the adverse effect of the chemotherapeutics.

With reference to the following examples, now the present invention will be further described in details. It is appreciated that the examples are illustrative but not limiting the scope of the present invention. For those experiment methods which were not noted with particular conditions, generally common conditions or the conditions suggested by the manufacturer would be referred.

EXAMPLE 1

The Preparation of Some Dimeric Phthalide Compound

The medical materials (chuanxiong rhizome or angelica, 100 kg) were extracted under reflux with 95% ethanol for 3 times, the filtrates were combined and concentrated, and then diluted with water to the alcohol concentration of about 80%. The mixture was extracted with petroleum ether for 3 times, the solvent was recovered until without alcohol smell. The resultant extracts were dissolved in water, and then extracted with ethyl acetate and n-butanol sequentially. The ethyl acetate fraction was removed off acid substances with 5% $NaHCO_3$ aqueous solution, washed with water to neutral, and concentrated into extracts. The extracts were loaded on the silica gel column and eluted with 20:1→10:1→5:1 petroleum ether and ethyl acetate. The $1^{st}$ to $5^{th}$ elutes were combined and repeatedly chromatograph purified by silica gel to obtain S3, i.e. the first peak in FIG. 1. The $20^{th}$ to $24^{th}$ elutes were combined and repeatedly chromatograph purified by silica gel, recrystallized with ethyl acetate to obtain S2 and S6, i.e. the $16^{th}$ and $17^{th}$ peak in FIG. 1. The $31^{st}$ elute was recrystallized with ethyl acetate to obtain S4 and S5, i.e. the $20^{th}$ and $15^{th}$ peak in FIG. 1. The $32^{nd}$ to $40^{th}$ elutes were combined and repeatedly chromatograph purified by silica gel to obtain S4 and S1, S1 was the $18^{th}$ peak in FIG. 1 (the method herein was referenced to Acta Pharmaceutica Sinica 2005, 40 (2): 141-144).

The resultant compounds S1-S6 were dimeric phthalide compounds.

S1:

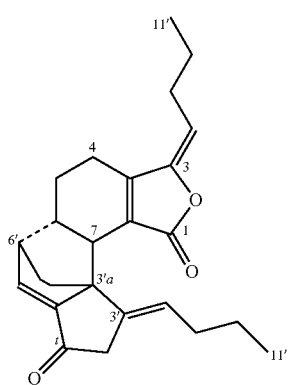

$^1$H-NMR (CDCl$^3$) δ2.02, 2.08 (1H, m, H-4, separately) 1.50, 1.91 (1H, m, H-5, separately) 2.55 (1H, t, J=7.8, H-6) 3.28 (1H, d, J=7.8, H-7) 5.58 (1H, t, J=8.1, H-8) 2.29 (2H, q, J=7.3, H-9) 1.46 (2H, m, H-10) 0.93 (3H, t, J=7.3, H-11) 1.4, 2.03 (1H, m, H-4') 1.30, 1.88 (1H, m, H-5') 2.99 (2H, m, H-6') 7.38 (1H, d, J=6.8, H-7') 5.0 (1H, t, J=7.6, H-8') 2.18 (2H, m, H-9') 1.45 (2H, m, H-9') 0.92 (3H, t, J=7.3)

$^{13}$C-NMR (CDCl$^3$) δ164.9 (C-1), 150.3 (C-3), 153.4 (C-3a), 22.2 (C-4), 29.0 (C-5), 38.3 (C-6), 41.5 (a, C-7), 129.6 (C-7a), 115.6 (C-8), 27.5 (C-9), 22.8 (C-10), 13.7 (b, C-11), 164.9 (C-1'), 150.4 (C-3'), 47.7 (C-3'a), 31.1 (C-4'), 25.7 (C-5'), 41.2 (a, C-6'), 142.0 (C-7'), 134.3 (C-7'a), 108.8 (C-8'), 27.8 (C-9'), 23.1 (C-10'), 13.9 (b, C-11')

S2:

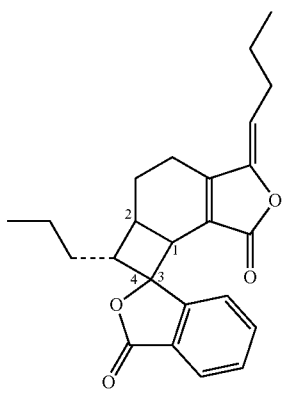

$^1$H-NMR (CDCl$^3$) α2.232, 2.635 (1H, m, H-4, separately) 2.18, 2.115 (1H, m, H-5, separately) 2.749 (1H, m, H-6) 3.659 (1H, d, J=8.2, H-7) 5.23 (1H, t, J=7.8, H-8) 2.33 (2H, m, H-9) 1.49 (2H, m, H-10) 0.95 (3H, t, J=7.4, H-11) 2.74 (1H, ddd, J=7.6, 1.0, 1.0, H-4') 7.74 (1H, ddd, J=7.6, 7.5, 1.0, H-5') 7.53 (1H, ddd, J=7.6, 1.0, 1.0, H-6') 7.83 (1H, ddd, J=7.6, 1.0, 1.0, H-7') 3.14 (1H, dt, J=7.8, 7.8, H-8') 1.44 (2H, m, H-9') 0.99 (2H, m, H-10') 0.76 (3H, t, J=7.4, H-11)

$^{13}$C-NMR (CDCl$^3$) δ168.5 (C-1), 149.4 (C-3), 154.8 (C-3a), 19.9 (C-4), 21.3 (C-5), 32.4 (C-6), 38.7 (C-7), 122.6 (C-7a), 112.2 (C-8), 28.1 (C-9), 22.5 (C-10), 14.3 (C-11), 170.3 (C-1'), 91.0 (C-3'), 151.1 (C-3'a), 121.0 (C-4'), 134.7 (C-5'), 129.7 (C-6'), 125.0 (C-7'), 125.7 (C-7'a), 47.6 (C-8'), 26.5 (C-9'), 20.8 (C-10'), 14.1 (C-11')

S3:

$^1$H-NMR (CDCl$^3$) δ2.01, 2.4 (1H, m, H-4, separately) 2.02, 2.6 (1H, m, H-5, separately) 2.89 (1H, dd, H-6) 3.54 (1H, d, J=10.0, H-7) 5.24 (1H, t, J=8.0, H-8) 2.4 (2H, m, H-9) 1.50 (2H, m, H-10) 0.95 (3H, t, J=7.5, H-11) 2.17 (1H, d, J=13.0, 3.0, H-3'α) 2.2 (2H, m, H-4') 2.1 (2H, m, H-5') 5.96 (1H, dt, J=10.0, 3.0, H-6') 6.14 (1H, dt, J=10.5, H-7') 1.84, 1.90 (1H, m, H-9', separately) 1.41, 1.53 (1H, m, H-10', separately) 1.00 (3H, t, J=7.0, H-11')

$^{13}$C-NMR (CDCl$^3$) δ167.9 (C-1), 147.8 (C-3), 155.5 (C-3a), 18.2 (C-4), 22.8 (C-5), 38.5 (C-6), 35.1 (C-7), 123.7 (c, C-7a), 113.4 (C-8), 28.0 (C-9), 22.3 (C-10), 13.9 (C-11), 170.3 (C-1'), 88.3 (C-3'), 44.5 (C-3'a), 22.4 (c, C-4'), 24.5 (C-5'), 130.8 (C-6'), 124.8 (C-7'), 49.7 (C-7'a), 207.9 (C-8'), 31.7 (C-9'), 15.5 (C-10'), 14.3 (C-11')

S4:

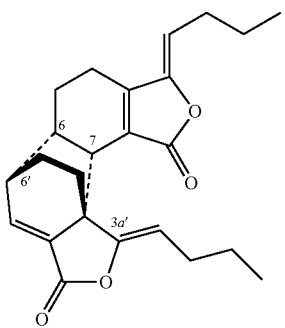

¹H-NMR (CDCl³) δ2.02, 2.18 (1H, m, H-4, separately) 1.50, 1.91 (1H, m, H-5, separately) 2.54 (1H, t, J=7.8, H-6) 3.25 (1H, d, J=7.8, H-7) 5.07 (1H, t, J=7.8, H-8) 2.30 (2H, q, J=7.3, H-9) 1.46 (2H, m, H-10) 0.93(3H, t, J=7.3, H-11) 1.34, 2.03 (1H, m, H-4') 1.30, 1.85 (1H, m, H-5') 2.99 (2H, m, H-6') 7.36 (1H, d, J=6.6, H-7') 5.0 (1H, t, J=7.6, H-8') 2.18 (2H, m, H-9') 1.45 (2H, m, H-9') 0.92 (3H, t, J=7.3)

¹³C-NMR (CDCl³) δ168.4 (C-1), 148.0 (C-3), 155.0 (C-3a), 19.8 (C-4), 29.0 (C-5), 38.3 (C-6), 41.6 (a, C-7), 126.6 (C-7a), 112.1 (C-8), 28.0 (C-9), 22.3 (C-10), 13.9 (b, C-11), 164.9 (C-1'), 150.5 (C-3'), 47.6 (C-3'a), 31.1 (C-4'), 25.8 (C-5'), 41.5 (a, C-6'), 142.0 (C-7'), 134.3 (C-7'a), 108.8 (C-8'), 27.5 (C-9'), 22.3 (C-10'), 13.8 (b, C-11')

S5:

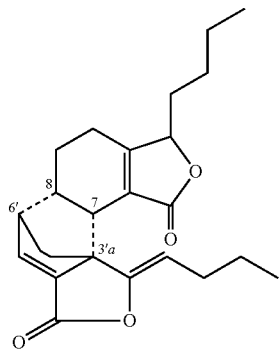

¹H-NMR (CDCl³) δ4.56 (1H, m, H-3) 1.98, 2.08 (1H, m, H-4, separately) 1.53, 1.90 (1H, m, H-5, separately) 2.54 (1H, m, H-6) 3.18 (1H, d, J=8.9, H-7) 1.38, 1.70 (1H, m, H-8, separately) 1.26 (2H, m, H-9) 1.45 (2H, m, H-10) 0.93 (3H, t, J=7.34, H-11) 1.40, 2.03 (1H, m, H-4', separately) 2.30, 1.87 (1H, m, H-5', separately) 2.97 (1H, m, H-6') 7.33 (1H, d, J=6.6, H-7') 4.98 (1H, t, J=7.3) 2.18 (2H, q, J=7.8, H-9') 1.44 (2H, m, H-10') 0.93 (3H, t, J=7.3, H-11')

¹³C-NMR (CDCl³) δ165.0 (C-1), 82.4 (C-3), 47.3 (C-3a), 30.9 (C-4), 25.7 (C-5), 41.6 (C-6), 141.9 (C-7), 134.5 (C-7a), 32.2 (C-8), 26.5 (C-9), 22.3 (C-10), 13.7 (C-11), 171.9 (C-1'), 150.5 (C-2'), 168.1 (C-3a), 22.4 (C-4'), 28.8 (C-5'), 38.3 (C-6'), 41.7 (C-7'), 127.1 (C-7'a), 108.6 (C-8'), 27.4 (C-9'), 22.2 (C-10'), 13.9 (C-11')

S6:

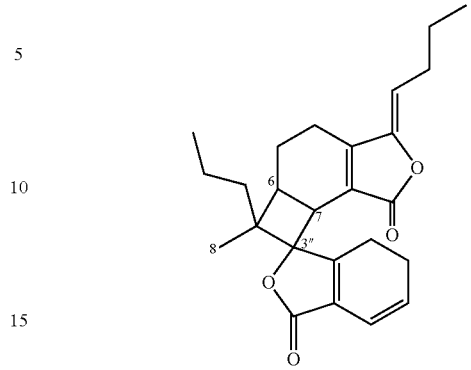

¹H-NMR (CDCl³) δ2.02, 2.57 (1H, m, H-4, separately) 2.02, 2.17 (1H, m, H-5, separately) 2.55 (1H, m, H-6) 3.47 (1H, d, J=7.3, H-7) 5.21 (1H, t, J=7.8, H-8) 2.33 (2H, m, H-9) 1.50 (2H, m, H1-10) 0.95 (3H, t, J=7.6, H-11) 2.58, 2.74 (1H, m, H-4', separately) 2.47, 2.75 (1H, m, H-5', separately) 5.93 (1H, dt, J=9.6, 4.1, H-6') 6.17 (1H, dt, J=9.6, 1.8, H-7') 2.94 (1H, q, J=7.8, H-8') 1.45 (2H, m, H-9') 1.14 (2H, m, H-10') 0.87 (3H, t, J=7.6, H-11')

¹³C-NMR (CDCl³) δ168.5 (C-1), 149.2 (C-3), 154.6 (C-3a), 19.6 (C-4), 26.2 (C-5), 35.0 (c, C-6), 44.0 (C-7), 122.3 (c, C-7a), 112.2 (C-8), 28.0 (C-9), 22.4 (C-10), 13.9 (C-11), 170.3 (C-1'), 92.0 (C-3'), 160.1 (C-3'a), 21.0 (c, C-4'), 20.7 (c, C-5'), 138.7 (C-6'), 117.0 (C-7'), 122.5 (d, C-7'a), 32.3 (c, C-8'), 20.0 (c, C-9'), 22.6 (C-10'), 14.1 (C-11')

The resultant S1-S6 dimeric phthalide compounds were ready for the following assays.

EXAMPLES 2-5

Evaluation of Cytology Efficacy

In the following Examples, the cell lines used were H1299, H446 (human lung cancer cell line), KB (human oral cavity carcinoma cell line), NB4, HL-60 (human leukemic cell line), U251 和U87MG (human glioblastoma cell line), MCF-7 (human breast carcinoma cell line), Bel-7402 and SMMC7721 (human hepatic cellular cancer cell line), SW620 (human colon carcinoma cell line), HDF (human dermis fibroblast), HUVEC (human umbilical vein endothelial cell line) and Kasumi-1 (human acute myeloid leukaemia cell line), all from American Type Culture Collection (ATCC).

HL-60/ADR, MCF-7/ADR, K562/ADR, Bel-7402/5-FU, KBV200, SMMC-7721/Adr were respectively chemotherapeutics Adriamycin (ADR), 5-Fluorouracil (5-FU) or vincristine (VCR) drug-resistant sub-stains of HL-60, MCF-7, K562, Bel-7402, KB, SMMC-7721 cells (all from Chinese Academy of Medical Sciences). NB4-R2 was all trans-retinoic acid (ATRA) drug-resistant sub-stain (from Pathophysiology Research Department of Shanghai JiaoTong University). The main drug-resistance mechanism of K562/ADR was high expression of P-glycoprotein (P-gp), along with increased expression of Bcl-2. In addition to high expression of P-gp, the drug-resistance mechanism of MCF-7/ADR also related to the high expression of Breast Cancer Resistant Protein (BCRP). The main drug-resistance mechanism of HL-60/ADR was high expression of Multidrug Resistance Protein 1 (MRP1), along with high expression of Bcl-2, Bcl-xL. The main drug-resistance mechanism of Bel-7402/5-FU was associated with the up-regulated expression of Glutathione S Transferase π (GST-π) and Bcl-xL. The main drug-resistance mechanism of KBV200 was high expression of P-gp and its increased activity. The drug-resistance mechanism of NB4-R2 on ATRA was mutation in the RAR gene locus.

EXAMPLE 2

Evaluation of Cytology Efficacy—The Inhibition Effects on Proliferation

The human lung cancer cell H1299 and H446, glioma cell U251 and U87MG, and human hepatic cellular cancer Bel-7402 cell in logarithmic growth phase were digested with pancreatic enzyme, and then suspended into DMEM or RPMI1640 containing 10% fetal bovine serum. The leukemic cells Kasumi-1 need no digestion, and were suspended into RPMI1640 containing 10% fetal bovine serum directly after centrifugalization. The cell density was adjusted to $1\times10^4$ cells/ml through cell counting, and the cell suspensions were seeded into a 96-well plate respectively, 100 μl/well, totally 6 groups of cells. The adherent cells were cultured overnight, the suspended cells were added different concentration gradients of dimeric phthalide compounds (S1-S6) directly, n=6 for each concentration of a single agent. The final volume was 200 ul, and the balance was supplemented with the culture medium. The plate was then incubated for 68 hours in 37° C., saturated humidity, 5% $CO_2$ cell incubator. The medium was aspirated and 72 μl/well fresh culture medium was added. 8 μl cholecystokinin-octopeptide (CCK-8) was added into each well and cultured for 2 hours. The absorbance was measured at 450 nm. The results were calculated as the 50% inhibiting drug concentration, i.e. IC50, using Sigmoidal simulation function by software Origin 7.0.

Figure 2:
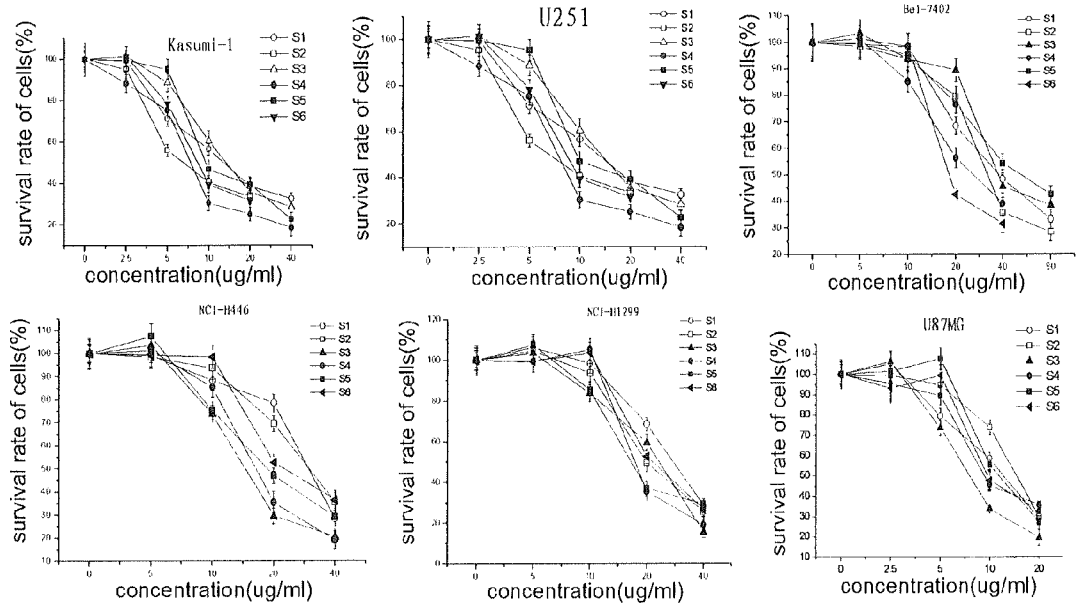
FIG. 2 shows the inhibition effect of the dimeric phthalide compound S1-S6 on the proliferation of various cell strains (Kasumi-1, U251, Bel-7402, NCI-H446, NCI-H1299 and U87MG).

The results are given in FIG. 2. The results have shown that S1-S6 have substantial inhibition effect on proliferation of various human cancer cells. Particularly, S4 demonstrated best inhibition effects on most of the cancer cells.

EXAMPLE 3

Overcome Drug Resistance of Different Mechanism

The cancer cells (various cell lines as shown in table 1 or FIG. 3) were seeded $1\times10^3$ cells per well into a 96-well plate. The suspended cells were added different concentration of dimeric phthalide compounds (S1-S6) directly, and the adherent cells were cultured overnight and added different concentration of dimeric phthalide compounds (S1-S6). The different concentration of dimeric phthalide compounds were divided into 10 groups: 0, 0.1, 0.5, 1, 5, 10, 20, 40, 80, 160 μg/ml, n=6 for each concentration.

According to the method described in Example 2, MTT was detected and $IC_{50}$ was calculated. The experiment was repeated for 3 times.

Figure 3:
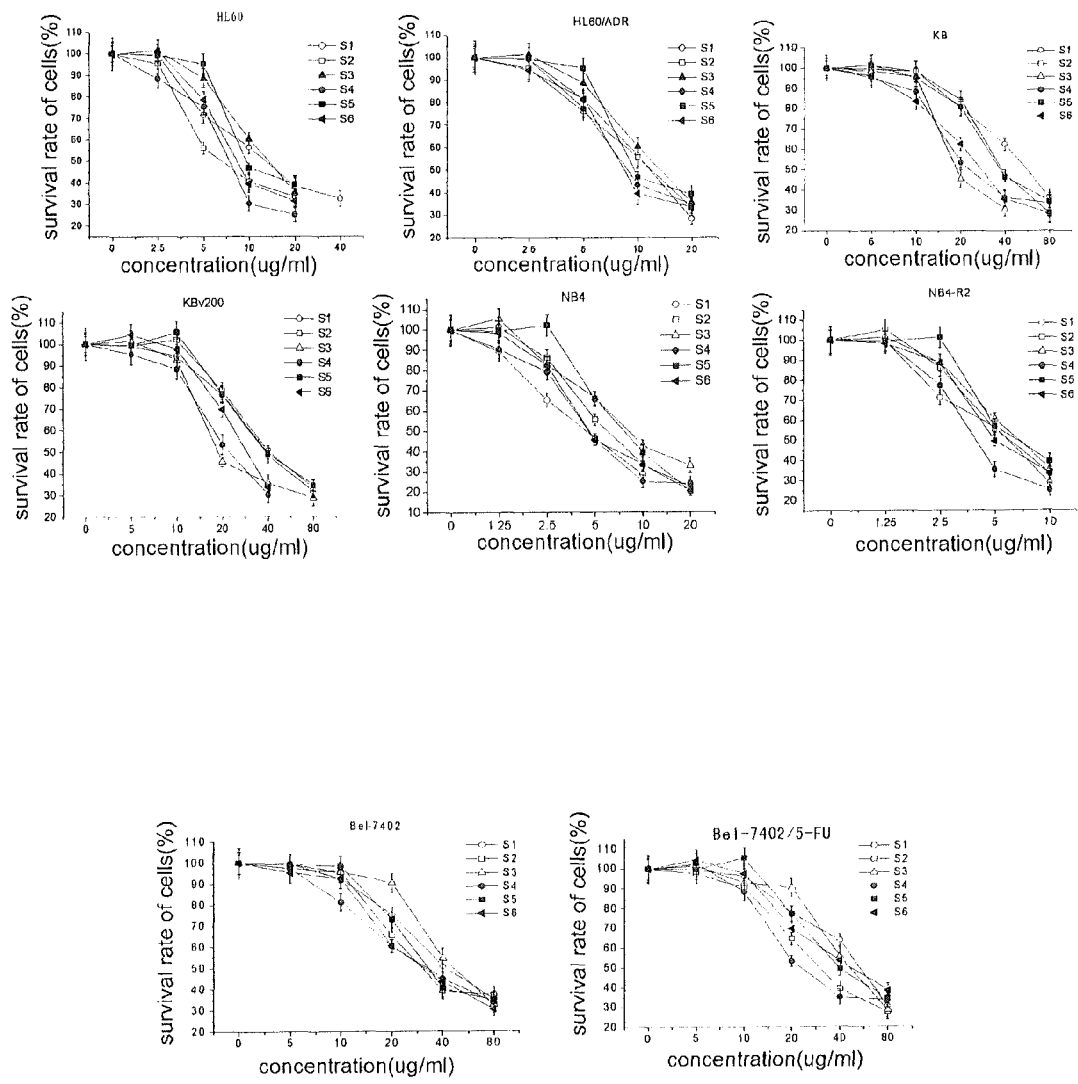
FIG. 3 shows the similar inhibition effect of the dimeric phthalide compound on the proliferation of drug resistant cell strains (HL60/ADR, KBv200, NB4-R2, Bel-7402/5-FU) and non drug resistant cell strains (HL60, KB, NB4, Bel-7402).

The growth inhibition effects of dimers of S1-S6 on its sensitive cell lines as well as the drug-resistant sub-strains ($IC_{50}$ (μg/ml)) were shown in table 1 and FIG. 3.

TABLE 1

| | cell | | | | | |
|---|---|---|---|---|---|---|
| | S1 | S2 | S3 | S4 | S5 | S6 |
| K562 | 19.034 ± 0.982 | 18.43 ± 1.020 | 17.43 ± 2.055 | 11.54 ± 0.8305 | 18.43 ± 0.8702 | 10.34 ± 0.597 |
| K562/Adr | 22.35 ± 1.092 | 20.44 ± 1.528 | 19.16 ± 1.707 | 12.38 ± 1.013 | 18.31 ± 0.762 | 11.78 ± 0.995 |
| KB | 19.43 ± 0.892 | 15.78 ± 1.252 | 19.04 ± 1.908 | 15.53 ± 3.220 | 16.40 ± 2.049 | 12.98 ± 2.504 |
| KBv200 | 20.67 ± 2.113 | 16.36 ± 1.980 | 20.44 ± 2.605 | 17.45 ± 2.032 | 19.83 ± 1.048 | 12.24 ± 2.151 |
| MCF-7 | 26.65 ± 1.053 | 25.63 ± 2.008 | 32.1 ± 3.209 | 18.45 ± 2.803 | 28.54 ± 1.907 | 22.43 ± 2.031 |
| MCF-7/Adr | 28.23 ± 1.107 | 29.45 ± 2.801 | 33.99 ± 3.063 | 20.32 ± 2.118 | 29.24 ± 2.143 | 24.50 ± 2.089 |
| Bel-7402 | 26.64 ± 3.208 | 27.87 ± 2.545 | 28.13 ± 3.963 | 16.43 ± 1.94 | 30.23 ± 2.165 | 22.59 ± 3.012 |
| Bel-7402/5-Fu | 32.33 ± 2.652 | 29.67 ± 1.985 | 29.32 ± 2.303 | 17.55 ± 3.676 | 28.07 ± 4.021 | 23.97 ± 2.656 |
| SMMC-7721 | 33.24 ± 3.421 | 37.85 ± 2.003 | 25.43 ± 1.995 | 19.42 ± 3.117 | 36.02 ± 3.922 | 23.98 ± 1.873 |
| SMMC-7721/Adr | 35.02 ± 2.872 | 38.31 ± 1.872 | 26.69 ± 2.600 | 22.66 ± 2.553 | 35.21 ± 2.330 | 22.98 ± 2.763 |

As shown in table 1 and FIG. 3, the dimeric phthalide compounds have similar efficacy on drug-resistant cells of different mechanisms as compared with sensitive cells, indicating that the compounds can effectively overcome tumor resistance of various resistance mechanisms, wherein S4 and S6 have the best effect.

EXAMPLE 4

Evaluation of Cytology Efficacy-Block Cell Cycle at G0/G1 Stage

The U87, HL-60 and H1299 were treated with S1-S6 at the concentration of 10 μg/ml and 20 μg/ml respectively for 48 h. And then $1\times10^6$ cells were collected, washed with PBS twice, fixed with 70% ethanol for 24 hours at 4° C. The cells were washed with PBS, and incubated with Tris-HCl buffers containing RNAase (pH 7.4) at 37° C. for 30 min. Then the cells were stained in dark for 30 min with propidium iodide (PI) to the final concentration of 50 μg/ml. The DNA content was detected by flow cytometry. The data were collected, stored and assayed by Modfit software (BD corporation).

Figure 4:
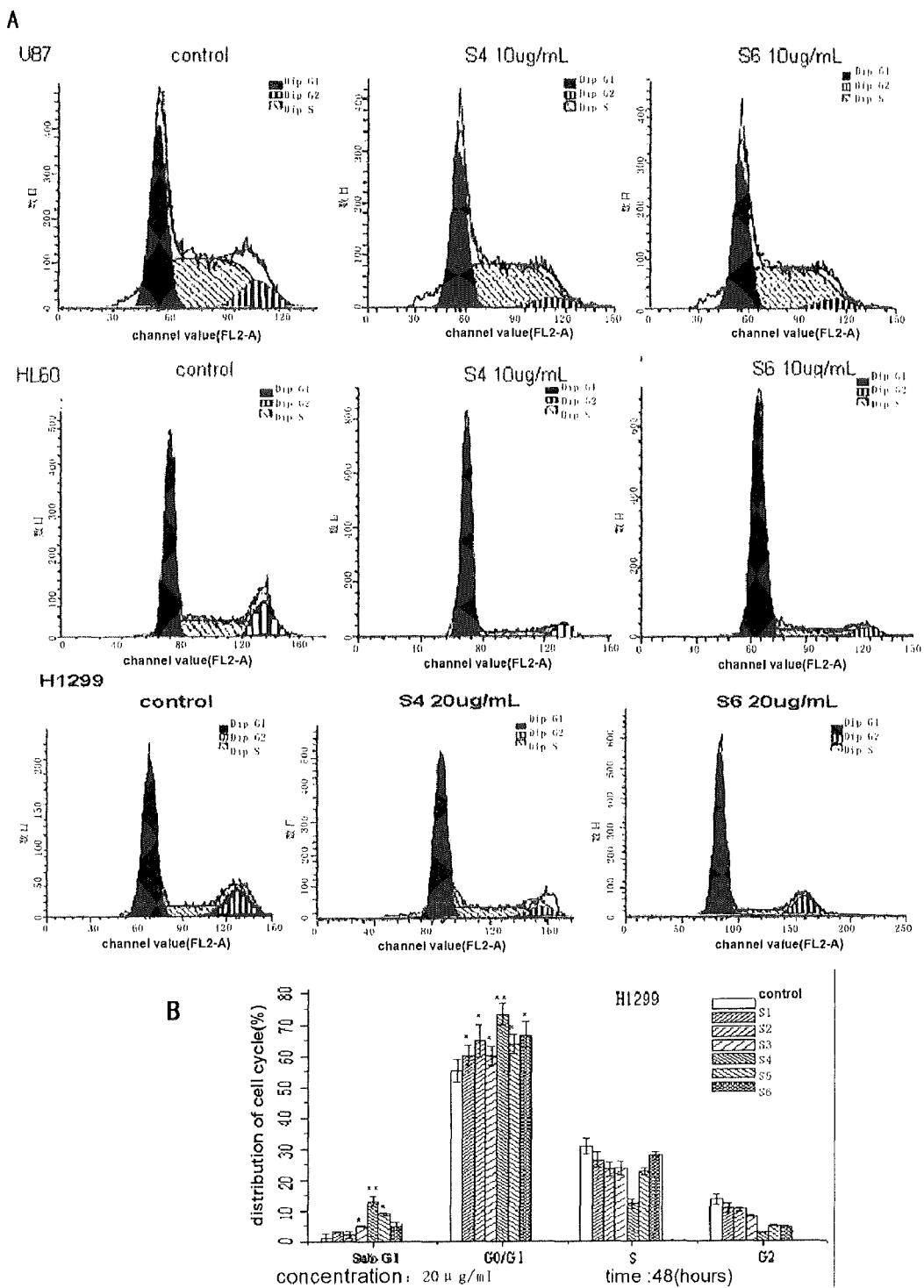
FIG. 4 shows that the dimeric phthalide compound can induce blocking effect of G0/G1 cell phase.

The results were shown in FIG. 4A and FIG. 4B. FIG. 4A was the flow cytometry graph obtained after treating U87, HL60 and H1299 with S4 and S6, control represent the flow cytometry graph of cells without treatment of dimeric phthalide compound; FIG. 4B was histogram of the cell cycle condition after treating H1299 cells with S1-S6 respectively, wherein the control represent the cell cycle condition of various cells without treating with dimeric phthalide compound.

As shown in the Figures, the dimeric phthalide compound have significant G0/G1 stage blocking effects on tumor cells.

EXAMPLE 5

Evaluation of Cytology Efficacy—Inducing Cell death

Figure 5:
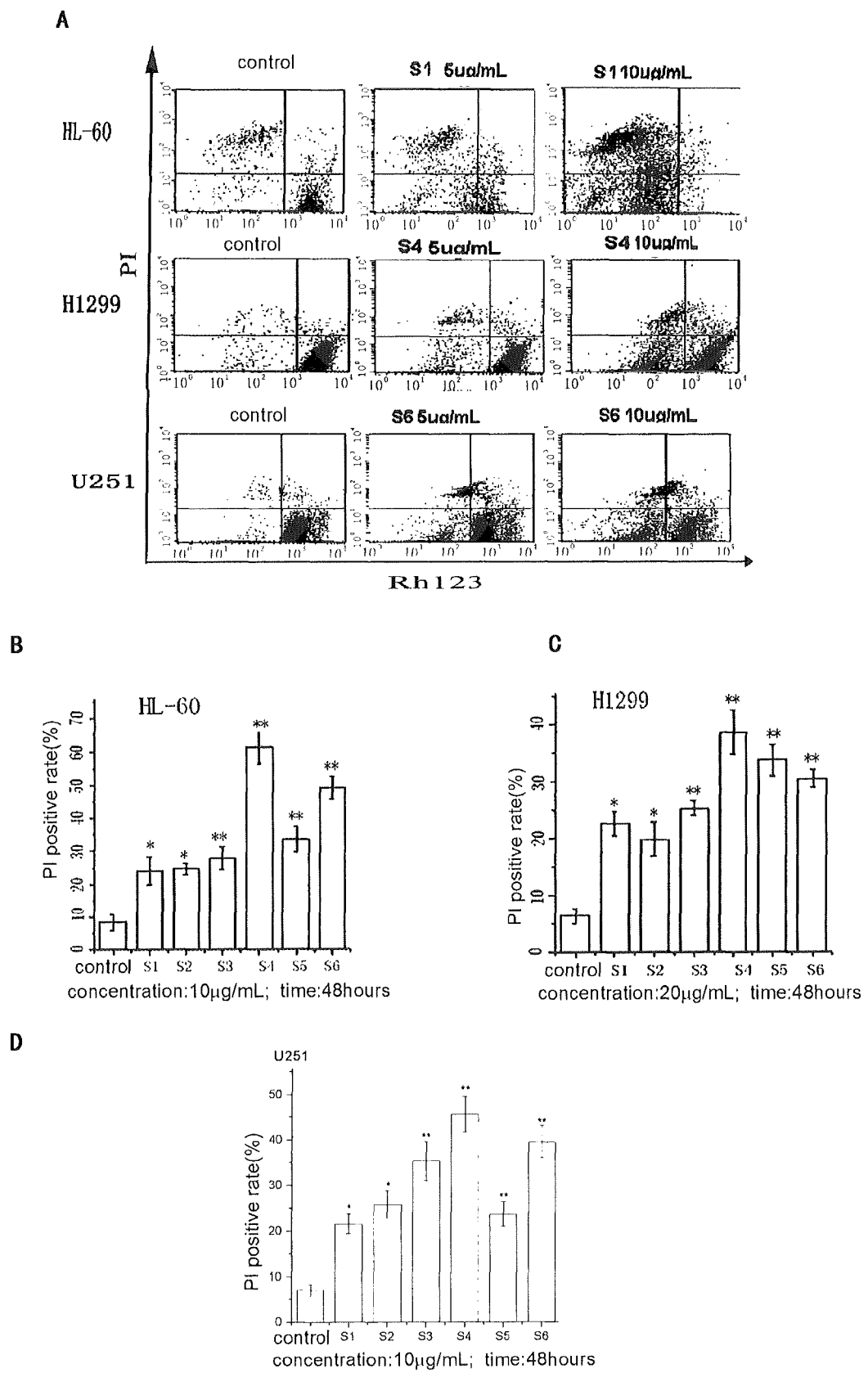
FIG. 5 show that the dimeric phthalide compound can induce death in various cell lines.

S1-S6 of different concentrations (as shown in FIG. 5) were added into HL-60, H1299, U251 cells under good growing conditions. The cells were cultured for 48 h, and collected. The cells were incubated with rhodamine 123 (Rh123) of the final concentration of 10 μg/ml for 20 min at 37° C., and then washed with pre-cooled PBS twice. The cells were suspended into PBS, and PI of final concentration of 25 μg/ml was added. After incubated in the dark at room temperature for 15 min, mitochondria membrane potential and PI positive cells were detected by flow cytometry, the death rate was calculated as the rate of PI positive cells.

The results were shown in FIG. 5. FIG. 5A was the flow cytometry graph of HL60, H1299 and U251 after treating with different concentration of S1, S4 and S6 respectively; FIG. 5B was the PI positive rate of HL60 after treating with S1-S6 (concentration 10 μg/mL, for 48 hours); FIG. 5C was the PI positive rate of H1299 after treating with S1-S6 (concentration 20 μg/mL, for 48 hours); FIG. 5D was the PI positive rate of U251 after treating with S1-S6 (concentration 10 μg/mL, for 48 hours). The control represented the corresponding results of cells without treating with dimeric phthalide compound.

As shown in the FIG. 5, the dimeric phthalide compound has significant effect of inducing the decrease of cell mitochondria membrane potential and cell death. S4 has the best effect of inducing cell death.

EXAMPLE 6

Inducing the Death of Drug-Resistant Cells of Different Mechanism

The dimeric phthalide compound S3, S4, S5, S6 (for concentrations, shown in FIG. 6A) were added into HL60, NB4, Bel-7402, KB under good growing conditions, as well as their drug resistant counterparts HL60/ADR, NB4-R2 Bel-7402/5-Fu, KBv200. The cells were cultured for 48 h, and collected. The cells were incubated with Rh123 of the final concentration of 10 μg/ml for 20 min at 37° C., and then washed with pre-cooled PBS twice. The cells were suspended into PBS, and PI of final concentration of 25 μg/ml was added. After incubated in the dark at room temperature for 15 min, they were detected by flow cytometry, and the results were listed in FIG. 6A.

The HL-60 cells were transiently transfected by eukaryotic expression vectors containing Bcl-2 and Bcl-xl for 24 h (the transfection agents were the Transfection 2000 kit from Invitrogen incorporation, as per the manufacturers' instruction) to form drug resistant cells with high expression of Bcl-2 or Bcl-xl. 15 μg/ml dimeric phthalide compound S4 were added and cultured for 24 h. The cells were collected and incubated with 10 μg/ml rhodamine 123 (Rh123) for 20 min at 37° C., and then washed with pre-cooled PBS twice. The cells were suspended into PBS, and PI of final concentration of 25 μg/ml was added. After incubated in the dark at room temperature for 15 min, they were detected by flow cytometry, and the results were listed in FIG. 6B.

Figure 6:
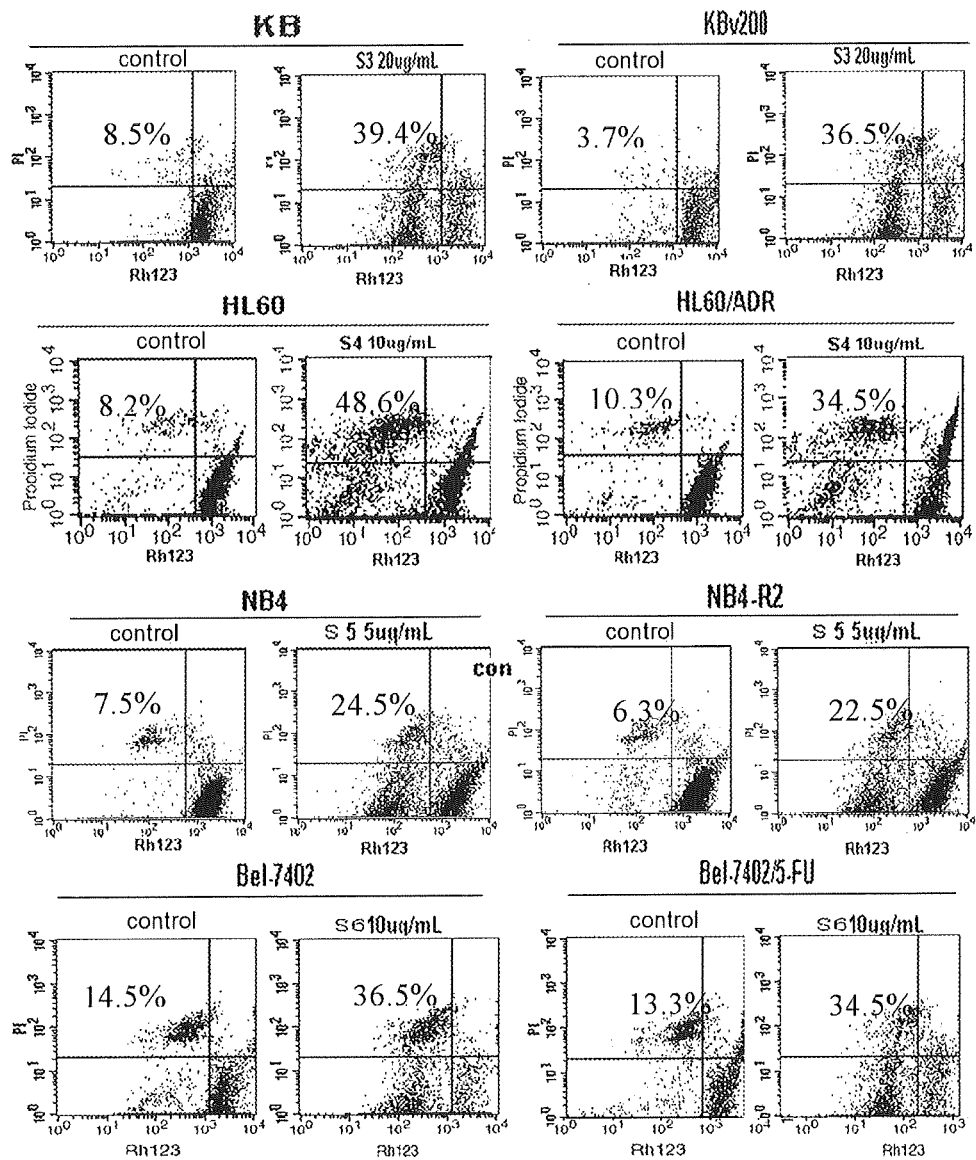
FIG. 6 shows a flow cytometry graph, demonstrating that the dimeric phthalide compound can induce death of non-drug resistant cells (KB, HL60, NB4, Bel-7402) as well as drug-resistant cells (KBv200, HL60/ADR, NB4-R2, Bel-7402/5-FU). Wherein, control represents a flow cytometry graph of cells without treating with dimeric phthalide compounds.
Figure 6:
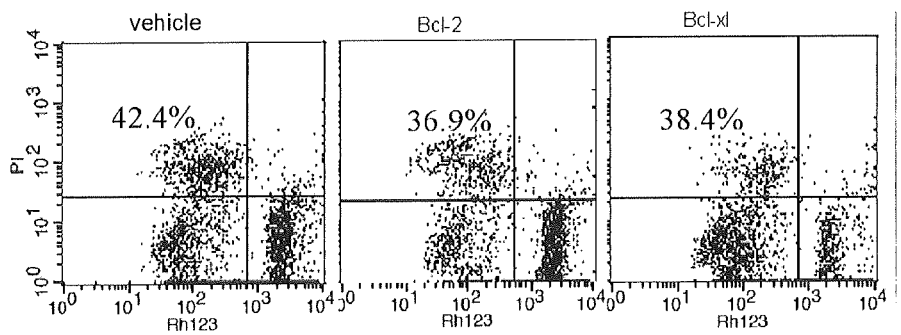

As shown in FIG. 6, the dimeric phthalide compound can induce similar effect of decreasing the cell mitochondria membrane potential and cell death (PI positive) between drug-resistant cells and non drug-resistant cells, demonstrating the compounds can over come drug resistance of different mechanisms.

EXAMPLE 7

The Molecular Mechanism of Inducing Cell Death-Inducing Mitochondrion Pathway Death The normal cells and treated cells were collected and extracted for mitochondrion and cytoplasm according to the instruction of cell components separation kit (Roche). The cell components were quantitated for the protein amount according to the general BCA method. An aliquot of protein was taken for 150 g/L SDS-PAGE electrophoresis. The proteins after separation were transferred onto cellulose nitrate filtration membrane and were blocked with 50 g/L defatted milk powder for 1 h. 1:200 dilution of murine anti-human cytochrome C(Cyto-C), apoptosis-inducing factor (AIF), poly-ADP ribose polymerase (PARP) were added, and IgG labeled with human HRP (1:200) was added. The mixture was incubated at room temperature for 2 h, and DAB colorated, Beta-Actin or GAPDH was used as control.

As shown in FIG. 7A, the dimeric phthalide compounds can induce Caspase activation by releasing mitochondria membrane proteins, resulting in the apoptosis or death of the tumor cells.

As shown in FIG. 7B, the mode of inducing death of the dimeric phthalide compounds is directly related with down regulating the anti-apoptosis proteins Bcl-2 and Mcl-1.

The cells were treated with the dimeric phthalide compounds, and meanwhile added or not added Caspase general inhibitor z-VAD-fmk (abbreviated as z-VAD or VAD; commercially from Chemicon Company, USA). The cells were detected for PI positive strain ratio by flow cytometry, the results were listed in FIG. 7C. As shown in FIG. 7C, the pre-treatment of Caspase general inhibitor z-VAD-fmk can partially inhibit the death of tumor cells (NB4) caused by the dimeric phthalide compounds, demonstrating that the cell death being inhibited was Caspase dependent death. In the Figures, "*" and "**" represent significant difference compared with the corresponding controls, P value<0.05 and <0.01 respectively; "+" and "++" represent significant difference compared with dimeric phthalide compound alone, P value<0.05 and <0.01 respectively.

As shown in FIG. 7D, the treatment of the dimeric phthalide compounds of HL60 cells resulted in release of Cyto-c, AIF along with activation of Caspase-9 and Caspase-3. Pre-treatment of Caspase inhibitor VAD can inhibit the activation of Caspase-9 and Caspase-3 caused by dimeric phthalide compound, but can not inhibit the release of Cyto-c, AIF caused by dimeric phthalide compound.

As shown in FIG. 7E, the pre-treatment of Caspase inhibitor VAD can not inhibit the death of tumor cells (HL60 and U87MG) caused by dimeric phthalide compound, suggesting a Caspase independent cell death. Wherein, "**" represent significant difference compared with corresponding control, P value<0.01.

Figure 7:
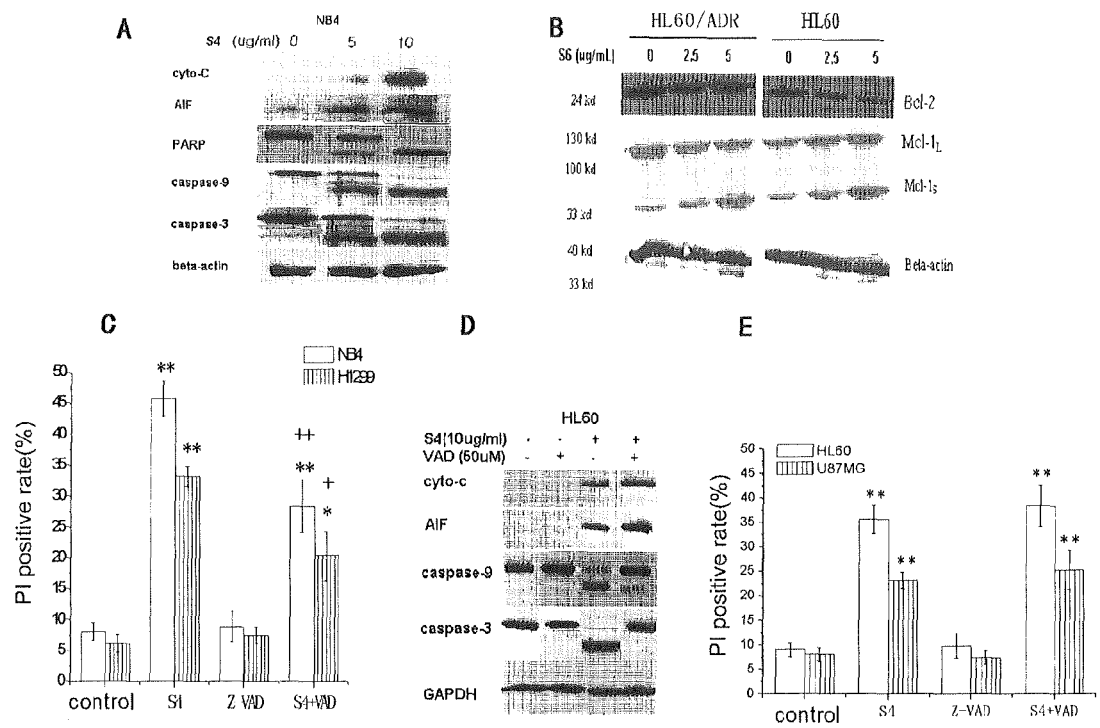
FIG. 7 shows that the dimeric phthalide compound can induce death of cancer cells through Caspase independent mitochondrion pathway.

In summary, FIG. 7 illustrated that the dimeric phthalide compounds may induce cell death through Caspase dependent or Caspase independent mitochondrion pathway. In addition, since H1299 was P53 deficient cell, which would not influence its sensitivity on dimeric phthalide compound, suggesting that the anticancer mechanism of the dimeric phthalide compounds was a P53 independent pathway.

EXAMPLE 8

Dimeric Phthalide Compounds Inhibit Vascular Proliferation

1. Vascular Endothelial Cell Inhibition Assay $2 \times 10^3$ cells were seeded into a 96-well plate and cultured for 24 h. S1-S6 of different concentrations (0, 0.01, 0.1, 0.5, 1, 2.5, 5, 10, 20, 40, 80, 160 μg/ml, respectively) were added and incubated for 72 h, n=6 for each concentration. The inhibition of cell proliferation was detected by CCK-8 assay, the results were calculated as IC50, as describe in Example 3.

As shown in table 2, HUVEC cells were strongly sensitive to all S1-S6 compounds, IC50 was between about 2.56 and 5.99, significantly lower than tumor cells and fibroblasts, and S1 had the best inhibition effect. These results illustrated that the dimeric phthalide compounds may preferential inhibit vascular endothelial cell, suggesting its excellent anti-angiogenesis effect.

TABLE 2

S1-S6 Preferential InhibitHUVEC (IC50; μg/ml)

| Compound | HUVEC | HDF | KB | Bel-7402 |
|---|---|---|---|---|
| S1 | 2.56 | 126.69 | 53.71 | 41.67 |
| S2 | 4.76 | 83.18 | 37.81 | 25.64 |
| S3 | 5.99 | 98.68 | 18.93 | 44.27 |
| S4 | 4.14 | 82.19 | 21.39 | 30.39 |
| S5 | 4.04 | 75.79 | 36.0 | 29.67 |
| S6 | 4.27 | 135.54 | 26.26 | 30.03 |

Assay of vascular endothelial cell growth factor (VEGF) in supernatant of tumor cell H1299 culture. The cell was seeded into a 24-well plate (n=3 for each sample). H1299 cell was treated with S1-S6 respectively and cultured for 24 h. The culture supernatants from each group were collected and operated according to the instruction of VEGF-ELISA kit (JIN MEI Corporation). The samples were added, incubated, washed and detected at 450 nm for OD values of each sample. The standard curve was obtained by using different dose of VEGF standards and the secretory volume of VEGF in the supernatant was calculated. The results were listed in table 3.

TABLE 3

Influence of S1-S6 on the secretion of VEGF in H1299 cell

| Compound (5 μg/ml) | Supernatant VEGF (ng/ml/$10^6$ cells) | Inhibition rate of VEGF secretion (%) |
|---|---|---|
| control | 373.2 ± 35.87 | 0 |
| S1 | 199.45 ± 28.12 | 46.54 |
| S2 | 245.71 ± 34.27 | 34.16 |
| S3 | 268.7 ± 36.13 | 28.0 |
| S4 | 234.00 ± 34.03 | 37.3 |
| S5 | 236.32 ± 24.02 | 36.7 |
| S6 | 237.25 ± 22.38 | 36.43 |

As shown in table 3, the dimeric phthalide compounds can significantly inhibit the secretion of vascular endothelial cell growth factor (VEGF) in tumor cells, wherein S1 demonstrated the most significant effect.

2. Inhibition on Chicken Embryo Allantocherion Blood Vessel

Figure 8:
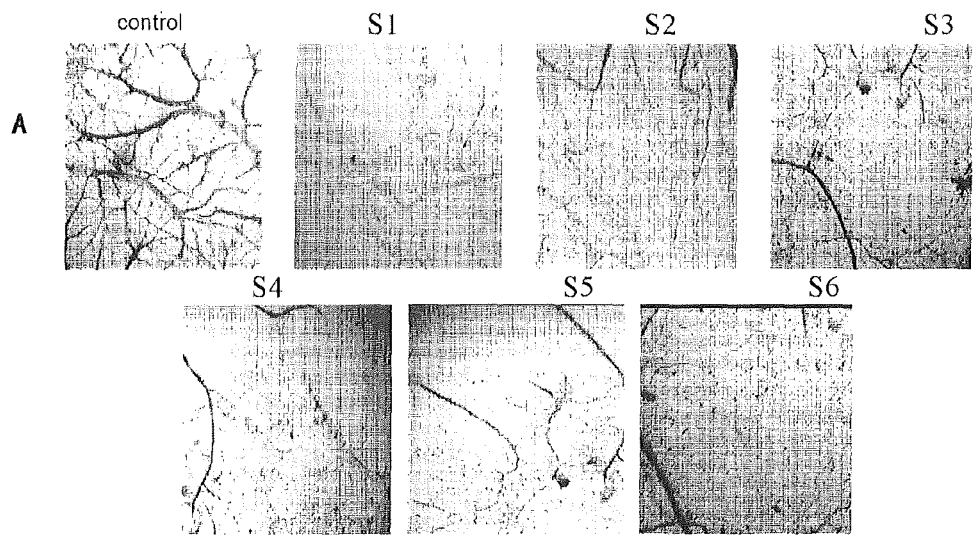
FIG. 8 show that the dimeric phthalide compound can suppress chicken embryo allantocherion neovascularization.

The fertilized eggs (N=70) were placed into a incubator at 37° C., RH55% and incubated for 8 days with the air-cell of eggs upward. The chicken embryo allantocherion (CAM) was exposed under sterile condition, and some disc cellulose dishes adsorbed with physiological saline, S1-S6 (5 μg/ml) were covered onto CAM, and the eggs were classified into 7 groups, 10 chicken embryo samples for each group. The openings were sealed with transfusion coatings and the eggs were put stand upward in an incubator at 37° C., RH55% for 3 days. The samples were fixed with 10% formaldehyde. CAM was cut in the center of the methyl cellulose membrane and put onto slides. The samples were dehydrated and counted under anatomical microscope for blood vessel branches in 4 visual fields. The inhibition rate of neovascularization was calculated according to the following equation: ((total blood vessel branches in control group-total blood vessel branches in treated group)/total blood vessel branches in control group)×100%. The results were shown in FIG. 8. FIG. 8A revealed the influence of S1-S6 on the blood vessel growth of chicken embryo allantocherion observed under microscope; FIG. 8B revealed the inhibition rate of neovascularization of different concentrations of S1-S6 compounds.

As shown in FIG. 8, the dimeric phthalide compounds can inhibit neovascularization, with S1 having the strongest effect. In conjunction of the results from table 2 and table 3, the inhibition mechanism of the dimeric phthalide compounds on neovascularization was associated with preferential inhibition of blood vessel endothelium proliferation, down regulation of VEGF secretion in tumor cells or blood vessel interstitial cells (chicken embryo).

EXAMPLE 9

In Vivo Evaluation of Tumor Inhibition: Inhibition of the Growth of Nude Mouse Heterograft Tumors Such as Human Nonsmall-Cell Lung Cancer/Liver Cancer/Glioma Experimental grouping: Balb/c male nude mice were used, each weighted 18-22 g, and three assays were performed. The mice were seeded with U87MG, H1299 and HL-60 respectively. The animals were divided into three groups for each experiment, one as control, one was administered with the dimeric phthalide compounds, and one was administered with monomers of phthalide compound, 6 animals for each group.

For the group which was administered with monomers of phthalide compound, we used n-butylidenephthalide (BP) (Sigma) as active ingredient for tumor suppression, the compound had the structure as follows:

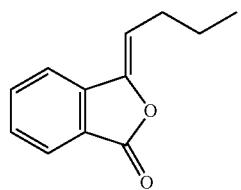

Experimental Process The H1299, HL-60 or U87MG cells growing in logarithmic phase were used. The cells were counted and made into single cell suspension with some DMEM or 1640 medium free of serum, the density of cells reached $1.5 \times 10^7$ ml. Each animal was inoculated subcutaneously in the right with 0.2 ml cell suspension, which is $3 \times 10^6$ cells/mouse. When the tumors had gown into 0.1-0.5 cm³ (about 7-10 days), the animals were intraperitoneal injected with the dimeric phthalide compound S4 (25 mg/kg), S6 (30 mg/kg), S1 (32 mg/kg), each 200 μl; for the group of monomers of phthalide compound, the mice were intraperitoneal injected with n-butylidenephthalide (250 mg/kg); the control group was administered with equal volume of vehicle. The animals were sacrificed after 4 weeks, and the subcutaneous tumors were separated. Photographs were taken (FIG. 9A) and the tumors were weighted (FIG. 9B).

Figure 9:
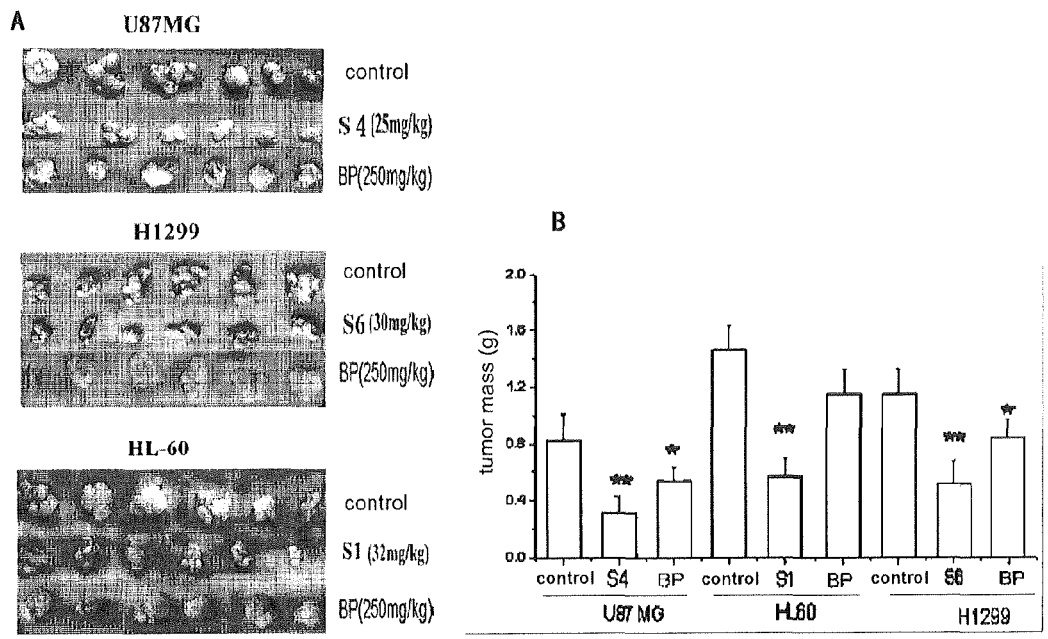
FIG. 9 shows the inhibition of different doses of dimeric phthalide compound and monomeric phthalide compound (n-butyl phthalide, BP) on the proliferation of Babl/C nude mouse heterograft tumor, wherein the control represents the status of mice intraperitoneal injected with equal volume of vehicle and caudal vein injected with equal volume of physiological saline.

As shown in FIG. 9, the dimeric phthalide compound (S4, S6 and S1) all had significant tumor inhibition effects, and could reach excellent effects with lower doses. Although the monomers of phthalide compound (BP) had some inhibition effects, the effects were not as significant as the dimeric phthalide compound, and needed much higher doses to reach similar effects (approximately 10 folds or higher) compared with the dimeric phthalide compound.

EXAMPLE 10

The Evaluation of Efficacy and Toxicity of the Combination of Dimeric Phthalide Compounds The Bel-7402 cells growing in logarithmic phase were used. The cells were counted and made into single cell suspension with some DMEM medium free of serum, the density of cells reached $1.5 \times 10^7$/ml. Each animal was inoculated subcutaneously in the right armpit with 0.2 ml cell suspension, which is $3 \times 10^6$ cells/mouse. 10 days after the inoculation, the animals were administered as follows.

Experimental group 1: intraperitoneal injected with 30 mg/kg S6 and caudal vein injected with physiologic saline;

Experimental group 2: caudal vein injected with 3 mg/kg vinblastine (VNB) and intraperitoneal injected with S6 vehicle;

Experimental group 3: intraperitoneal injected with 30 mg/kg S6 and caudal vein injected with 3 mg/kg VNB at the same time;

Control: intraperitoneal injected equal volume of vehicle and caudal vein injected with equal volume of physiologic saline.

Each group included 6 nude mice, and their weight variations (see FIG. 10A) and tumor sizes (see FIG. 10B) were detected during the experimental process. In FIG. 10B, "**" represent significant difference compared with the control group, P value<0.01.

Figure 10:
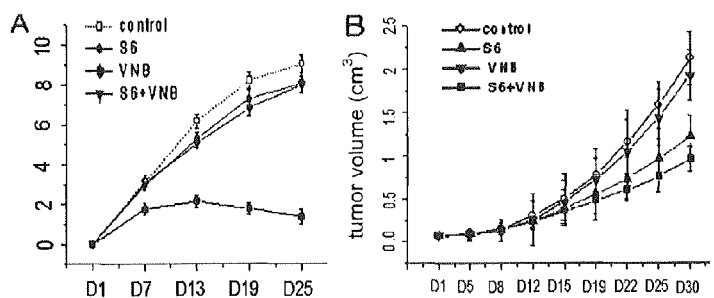
FIG. 10 shows the effect of the dimeric phthalide compounds, wherein D1, D5, . . . , D30 represent days after administration; control represents the status of mice intraperitoneal injected with equal volume of vehicle and caudal vein injected with equal volume of physiological saline.

As shown FIG. 10, there was no significant toxicity for S6 group, while VNB has significant adverse effects (substantially weight loss). The combination of S6 and VNB could not only increase efficacy but also decrease the weight loss caused by VNB.

The references cited herein are incorporated by reference in their entireties for all purposes to the same extent as if each individual reference has been individually indicated to be incorporated by reference for all purposes. In additional, it will be clear to one skilled in the art from a reading of this disclosure that various changes in form and detail can be made without departing from the true scope of the invention. These variations and modification will also fall into the scope defined by the attached claims.

The invention claimed is:

1. A method of treating a subject having a tumor that is resistant to a drug, comprising:
administering to a subject having a tumor that is resistant to a drug an amount of a dimeric phthalide compound having one of the following formulas (1) and (16),

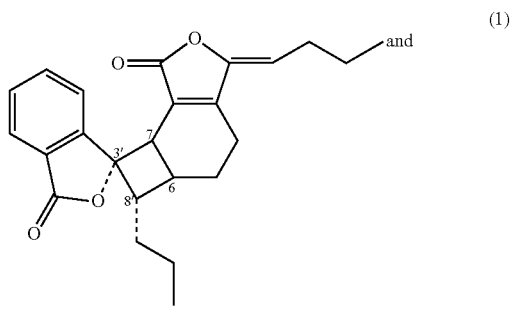

(1)

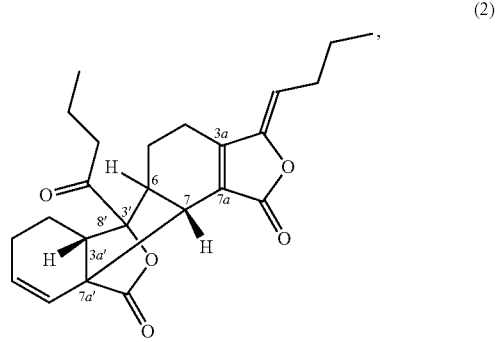

(2)

wherein the amount of the dimeric phthalide compound is an amount effective for treating the tumor that is resistant to the drug.

2. The method of claim 1, wherein the amount of the dimeric phthalide compound is effective for directly inhibiting proliferation of tumor cells, directly inducing cell death, or indirectly inhibiting development of a tumor by suppressing tumor angiogenesis.

3. The method of claim 1, wherein the tumor that is resistant to the drug or the tumor that is resistant to apoptosis is selected from the group consisting of nonsmall-cell lung cancer, liver cancer, encephaloma, leukocythemia, carcinoma of prostate, intestine cancer, myeloma tumor, lymphoma, breast carcinoma, ovarian cancer, gastric cancer, small cell lung cancer, esophageal carcinoma, esophageal carcinoma, and sarcoma.

4. The method of claim 1, wherein the amount of the dimeric phthalide compound is effective for increasing an efficacy of chemotherapeutics, and/or decreasing toxicity of chemotherapeutics.

5. The method of claim 1, further comprising administering an anti-tumor drug.

6. The method of claim 5, wherein the anti-tumor drug includes at least one selected from the group consisting of a targeting drug, a cytotoxic drug, or a differentiation inductor.

7. The method of claim 1, wherein the subject having the drug resistant tumor is a subject that exhibits at least one of the following: (1) overexpression of P-glycoprotein (P-gp), (2) overexpression of Bcl-2, (3) overexpression of Breast Cancer Resistant Protein (BCRP), (4) overexpression of Multidrug Resistance Protein 1 (MRP1), (5) overexpression of Bcl-xL and overexpression of Glutathione S Transferase $\pi$ (GST-$\pi$).

8. The method of claim 1, wherein the drug is at least one anti-tumor drug selected from the group consisting of a targeting drug, a cytotoxic drug and a differentiation inductor.

9. The method of claim 8, wherein the targeting drug is gifitinib, erlotinib, sorafenib or bevacizumab and the cytotoxic drug is vinblastine, anthracycline, an antibiotic or a metabolic drug.

10. The method of claim 1, wherein the amount of the dimeric phthalide compound is effective for inducing a decrease of cell mitochondria membrane potential and cell death.

* * * * *